US00PP32982P2

(12) United States Plant Patent
Olesen

(10) Patent No.: US PP32,982 P2
(45) Date of Patent: Apr. 20, 2021

(54) VARIETY DENOMINATION 'POULPAH097'

(50) Latin Name: *Rosa hybrida*
Varietal Denomination: Poulpah097

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,982

(22) Filed: Sep. 3, 2020

(51) Int. Cl.
*A01H 6/74* (2018.01)
*A01H 5/02* (2018.01)

(52) U.S. Cl.
USPC ..... Plt./118

(58) Field of Classification Search
USPC ..... Plt./118
See application file for complete search history.

*Primary Examiner* — Annette H Para

(57) ABSTRACT

A new garden rose plant of the miniature class which has abundant, yellow flowers and attractive foliage. This new and distinct variety has shown to be uniform and stable in the resulting generations from asexual propagation.

3 Drawing Sheets

Botanical designation: *Rosa hybrida.*
Variety denomination: 'Poulpah097'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah097', originated as a single seedling from the stated cross.

The new variety may be distinguished from its male pollen parent and female seed parent primarily by the following characteristics. The male pollen parent plant has apricot flowers while the new variety has yellow flowers. The female seed parent plant has large diameter yellow flowers of about 60 mm while the new variety has yellow flowers with a diameter of 45 to 50 mm.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpah097' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah097' was selected in the spring of 2011 by the inventor as a single plant from the progeny of the aforementioned hybridization.

Asexual reproduction of 'Poulpah097' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpah097' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah097'.

Specifically illustrated in FIG. 1 of the drawings are open flowers, viewed from above and laterally, sepals detached, showing foliaceous appendages and receptacle, flower petals detached revealing reproductive flower parts.

Figure 1:
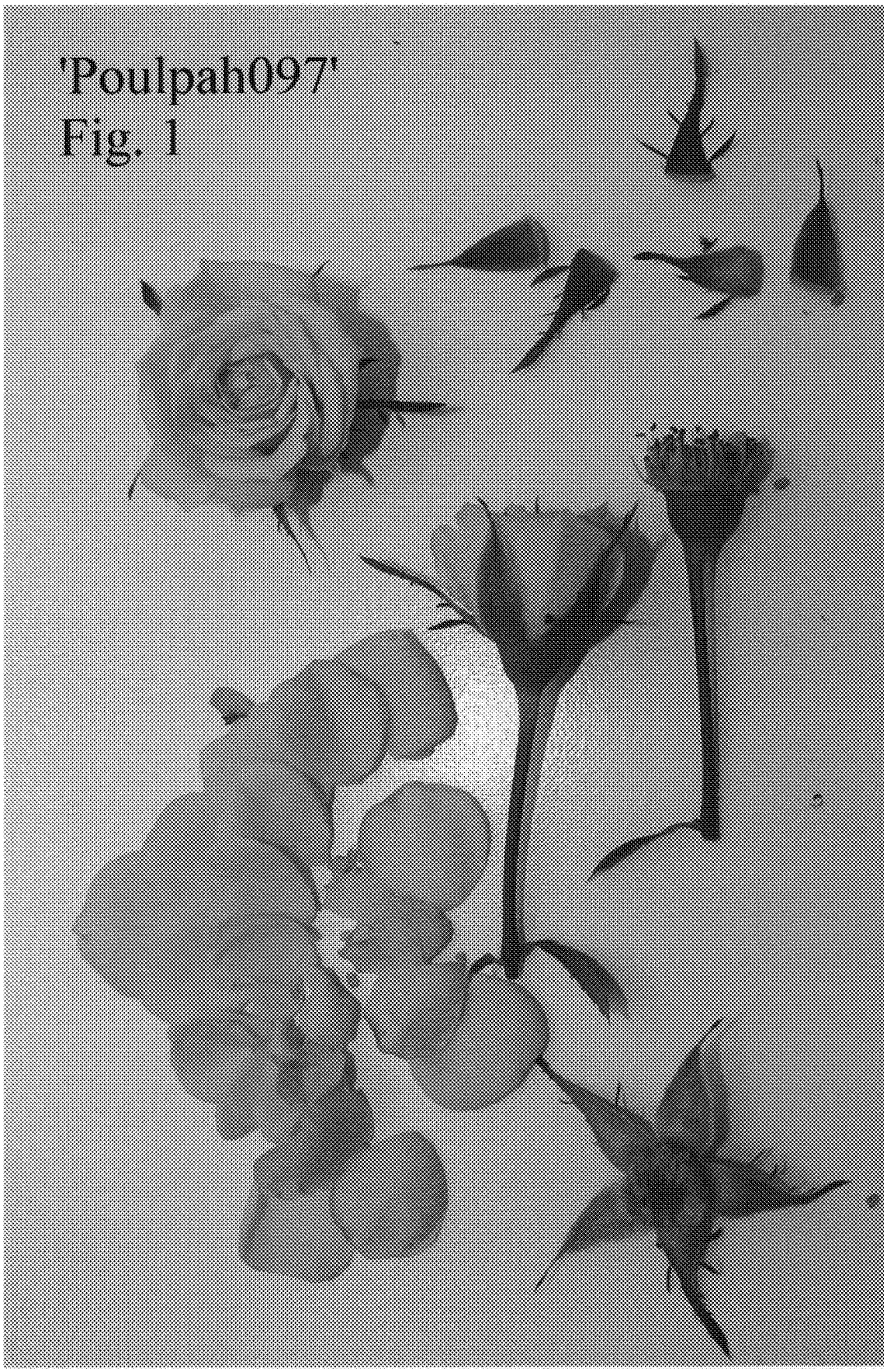
Figure 2:
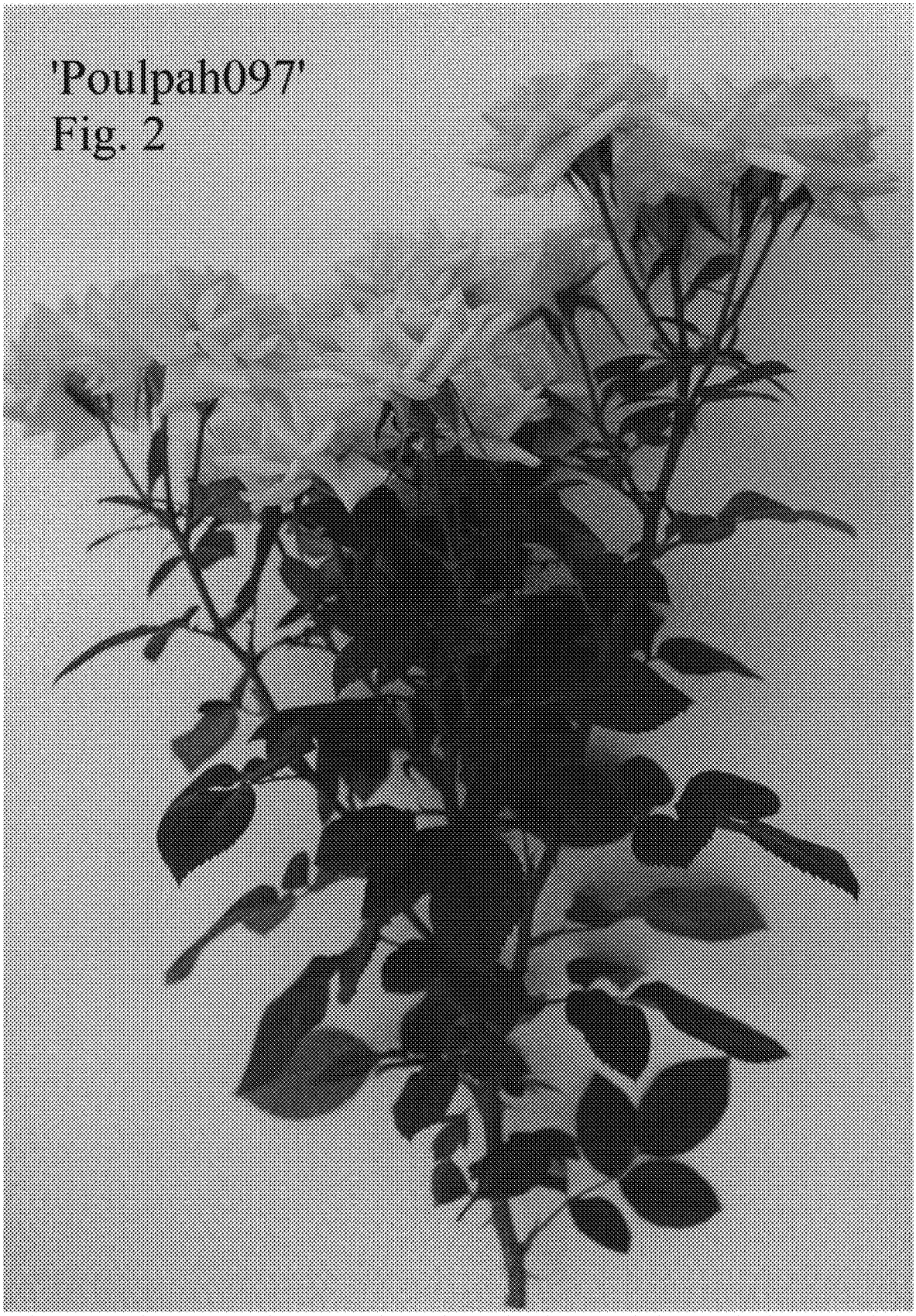

Specifically illustrated in FIG. 2 of the drawings is a flowering branch of 'Poulpah097' showing arrangement of open flowers on peduncles.

Figure 3:
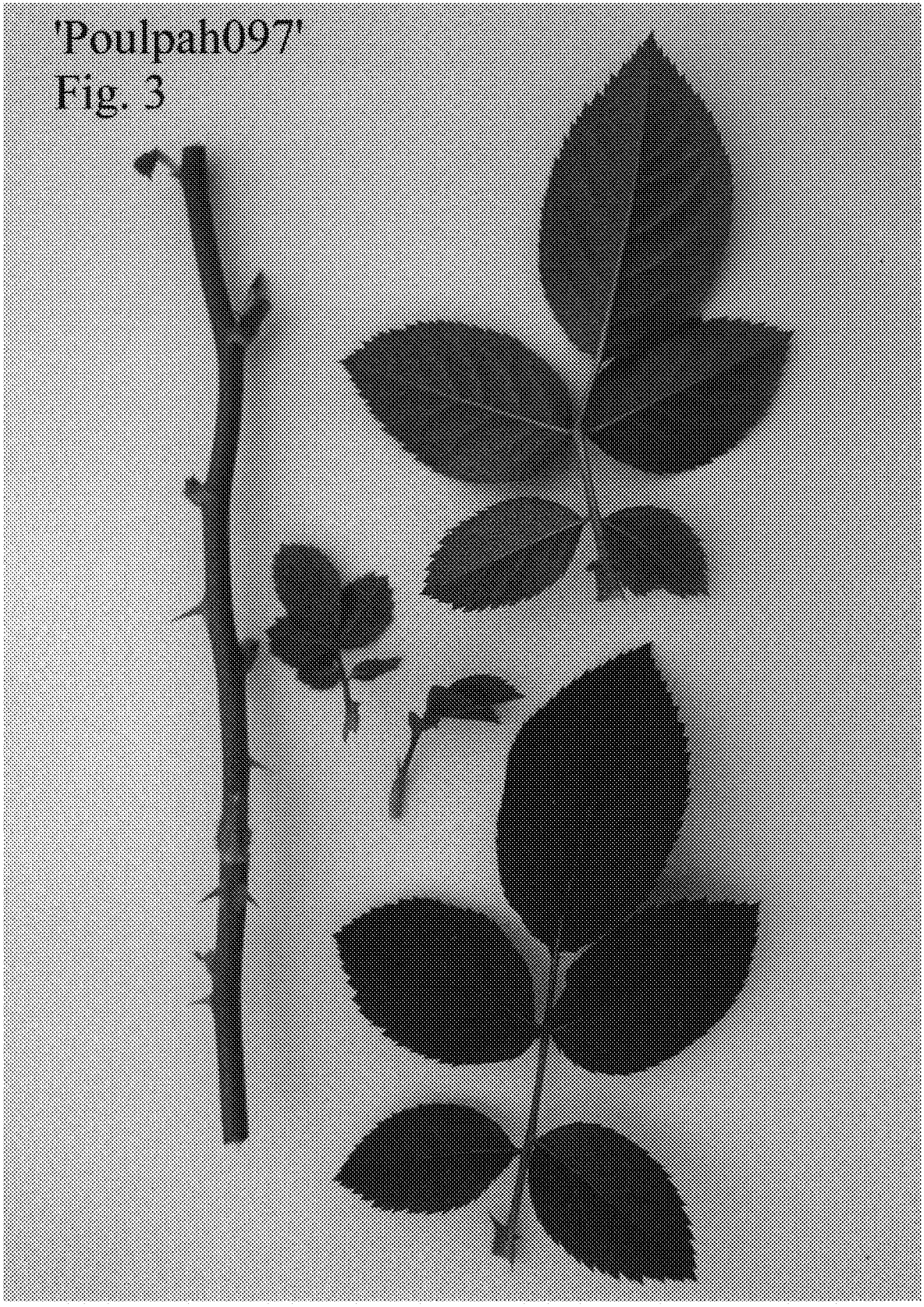

Specifically illustrated in FIG. 3 of the drawings are mature and juvenile foliage, and a bare stem exhibiting prickles. Plants shown are 2 years of age.

DETAILED DESCRIPTION OF THE VARIETY

The following is a description of 'Poulpah097', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah064', U.S. Plant Pat. No. 25,971 are compared to 'Poulpah097' in Chart 1.

CHART 1

| | 'Poulpah097' | 'Poulpah064' |
|---|---|---|
| Petal Count | 37 | 35 |
| Flower Diameter | 45 to 50 mm | 60 mm |
| General Tonality of Flower Color | Yellow Group 9A | Yellow-Orange Group 14C with other intonations of Yellow-Orange Group 22B |

FLOWER AND FLOWER BUD

Blooming habit: Continuous.

Flower bud:

*Size*.—Upon opening, 20 mm in length from base of receptacle to end of bud. Bud diameter is 15 mm.

*Bud form*.—Ovoid.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—29 mm long, 10 mm wide.

*Receptacle*.—Texture: Smooth. Size: 6 mm in height, 9 mm wide. Color: Yellow-Green Group 144A. Shape: Campanulate.

*Pedicel*.—Surface: Smooth. Length: 36 mm. Diameter: 3 mm on average. Color: Yellow-Green Group 144A. Strength: Strong.

*Peduncle*.—Length: 3 to 6 cm. Diameter: About 3 mm. Color: Yellow-Green Group 145A. Texture: Smooth.

Flower bud development: Flower buds are borne in clusters of 3 to 5 flower buds on each peduncle.

Flower bloom:

*Fragrance*.—Light floral.

*Duration*.—The blooms have a duration on the plant of approximately 21 days. Petals fall cleanly away from plant after flowers have fully matured.

*Size*.—Flower diameter is 45 to 50 mm when open. Flower depth is 18 mm.

*Flower shape*.—High centered, double, with a high pointed center which is tightly closed.

*Shape of flower, side view*.—The upper portion is flat. The lower portion is flat.

Petalage: Under normal conditions, flowers have about 37 petals.

General tonality of flower: Open flowers are Yellow Group 9A.

Petal color:

*Upon opening, outer petals*.—Upper surface: Yellow Group 9A. Lower surface: Yellow Group 12B.

*Upon opening, inner petals*.—Upper surface: Yellow Group 9A. Lower surface: Yellow Group 12B.

*Basal petal spots*.—Upon opening there is no distinctive coloration at the petal base observed.

*After opening, outer petals*.—Upper surface: Yellow Group 10B. Lower surface: Yellow Group 10D.

*After opening, inner petals*.—Upper surface: Yellow Group 10B. Lower surface: Yellow Group 10D.

*Basal petal spots*.—After opening there is no distinctive coloration at the petal base observed.

Petals:

*Petal reflex*.—Slight to strong as flowers mature.

*Margin*.—Entire and uniform. Slight point at apex of some petals. No undulations.

*Shape*.—Elliptical Apex shape: Rounded. Base shape: Acute.

*Size*.—About 21 mm (l)×23 mm (w).

*Texture*.—Smooth.

*Thickness*.—Average.

Petaloids:

*Size*.—12 mm (l) by 8 mm (w).

*Quantity*.—About 7.

*Shape*.—Elliptical with an acute base and rounded apices.

*Color*.—The upper side is Yellow Group 9A. The lower side is Yellow Group 12B.

Reproductive flower parts:

*Pollen*.—None observed.

*Anthers*.—Size: 1.5 mm in length. Color: Greyed-Orange Group 163C. Quantity: 48 on average.

*Filaments*.—Color: Yellow Group 12A. Length: 5 mm.

*Pistils*.—Length: 4 mm. Quantity: 30 on average.

*Stigmas*.—Color: Greyed-Yellow Group 160C.

*Styles*.—Color: Red-Purple Group N57B.

*Location of stigmas*.—Inferior in location relative to the length of the filaments and the height of the anthers.

*Hips*.—None Observed.

PLANT

Plant growth: Upright, and well branched. Plants are about 50 cm in height, and 45 cm wide.

Stems:

*Color of juvenile growth*.—Yellow-Green Group 144B.

*Color of mature growth*.—Yellow-Green Group 144A.

*Length*.—Canes are about 25 to 30 cm from the base of the plant to the flowering portion.

*Diameter*.—About 5 mm.

*Internodes*.—On mature canes about 30 mm between nodes.

*Surface texture*.—Young wood: Smooth. Older wood: Smooth.

Long prickles:

*Incidence*.—7 prickles per 10 cm of stem.

*Size*.—Average length of prickles on mature stems is 9 mm.

*Shape*.—Upper portion is linear. Lower portion is concave.

*Color*.—Juvenile prickles: Greyed-Yellow Group 160C. Mature prickles: Greyed-Yellow Group 160C.

Plant foliage:

*Compound leaf*.—About 103 mm (l)×80 (w).

*Quantity*.—3 leaves per 10 cm of stem on average.

*Leaf bearing angle to the stem*.—45 degrees.

*Color of juvenile foliage*.—Upper side: Yellow-Green Group 144A with intonations of Greyed-Red Group 179A. Lower side: Yellow-Green Group 144A with intonations of Greyed-Red Group 179A.

*Color of mature foliage*.—Upper side: Yellow-Green Group 147A. Lower side: Yellow-Green Group 147C.

Plant leaves and leaflets:

*Stipules*.—Size: 7 mm long, mm wide. Quantity: 2 per compound leaf. Shape: Linear, slightly broad based with outward extending apices. Margins: Finely serrated. Color: Yellow-Green Group 144A.

*Petiole*.—Length: 10 mm. Diameter: About 2 mm. Upper surface color: Yellow-Green Group 144A. Lower surface color: Yellow-Green Group 144A.

*Rachis*.—Length: About 26 mm. Upper surface color: Yellow-Green Group 144A. On juvenile leaves Greyed-Red Group 179A. Lower surface color: Yellow-Green Group 144A.

*Leaflet*.—Quantity: Normally 5 leaflets. Margins: Serrated. Size: Terminal leaflets are about 50 mm long, 30 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah097', substantially as illustrated and described herein, due to its abundant yellow flowers, disease resistance, and extended period of bloom.

* * * * *

'Poulpah097'

'Poulpah097'

'Poulpah097'